United States Patent [19]

Schön et al.

[11] Patent Number: 5,354,923
[45] Date of Patent: Oct. 11, 1994

[54] PROCESS FOR THE PREPARATION OF AROMATIC CARBONIC DIESTERS

[75] Inventors: Norbert Schön; Hans-Josef Buysch, both of Krefeld; Eberhard Zirngiebl, Cologne; Jürgen Kischkewitz, Ratingen, all of Fed. Rep. of Germany

[73] Assignee: Bayer Aktiengesellschaft, Leverkusen, Fed. Rep. of Germany

[21] Appl. No.: 788,959

[22] Filed: Nov. 7, 1991

[30] Foreign Application Priority Data

Nov. 16, 1990 [DE] Fed. Rep. of Germany ....... 4036594

[51] Int. Cl.$^5$ ................. C07C 68/06; C07C 69/96
[52] U.S. Cl. ................... 558/270; 558/260; 558/273; 558/274; 423/610
[58] Field of Search ............. 558/260, 270, 273, 274; 423/610

[56] References Cited

U.S. PATENT DOCUMENTS

| | | | |
|---|---|---|---|
| 4,252,737 | 2/1981 | Krimm et al. | 558/274 |
| 4,929,764 | 5/1990 | Hargis | 564/399 |
| 4,937,062 | 6/1990 | Jordan et al. | 423/592 |
| 5,149,856 | 9/1992 | Schon et al. | 558/270 |

FOREIGN PATENT DOCUMENTS

| | | |
|---|---|---|
| 2710630 | 9/1978 | Fed. Rep. of Germany . |
| 54-125617 | 9/1979 | Japan . |
| 0025138 | 3/1981 | Japan ................. 558/270 |
| 0176932 | 10/1982 | Japan ................. 558/270 |
| 0183745 | 11/1982 | Japan ................. 558/270 |

OTHER PUBLICATIONS

Abstract of Japanese Patent No. 54-125,617, Oct. 14, 1986.
Tang et al, "Preparation and Properties of Sulfate Zirconia and Titania Catalysts", Hangzhou Daxue Kuebue 14(3), 323-8, CA108(16): 138515b. Abstract & Citation only.

*Primary Examiner*—José G. Dees
*Assistant Examiner*—Keith MacMillan
*Attorney, Agent, or Firm*—Sprung Horn Kramer & Woods

[57] ABSTRACT

Carbonic diesters containing at least one aromatic ester group can be prepared from carbonic diesters containing at least one aliphatic ester group by transesterification using a phenol, titanium dioxide having a surface area of at least 20 m$^2$/g as determined by the BET method being used as catalyst.

10 Claims, No Drawings

PROCESS FOR THE PREPARATION OF AROMATIC CARBONIC DIESTERS

The invention relates to a process for the preparation of aromatic carbonic diesters by catalysed transesterification, in which titanium dioxides are used as catalysts.

The preparation of aromatic and aliphatic-aromatic carbonic diesters by transesterification starting from aliphatic carbonic esters and phenols, is known in principle. This reaction is an equilibrium reaction in which the position of the equilibrium has almost completely been shifted towards the aliphatically substituted carbonic esters. It is therefore relatively easy to prepare aliphatic carbonic diesters from aromatic carbonic esters and alcohols, while the reverse reaction is only successful if very reactive and selective catalysts are available.

For the purpose mentioned, a plurality of homogeneously soluble catalysts or catalysts which go homogeneously into solution during the reaction are known, for example Lewis acid catalysts from the group comprising metal halides or suitable acyloxy, alkoxy and aryloxy compounds of Al, Ti, U, V, Zn, Fe and Sn (DE-OS (German Published Specification) 2,528,412 and 2,552,907) or tin compounds of the formula —$R_2SnO$— (DE-OS (German Published Specification) 3,445,552).

It was therefore desired to find heterogeneous catalysts which have a sufficiently reactive and selective effect in the transesterification process according to the invention. Such heterogeneously or solid-phase-bound transesterification catalysts would have the advantage that they could be separated off from the products without problems after the reaction is complete or could advantageously be used in a continuously operating process.

Heterogeneous transesterification catalysts for the transesterification mentioned consisting of mixed oxides of silicon and titanium, prepared by joint hydrolysis of silicon halides and titanium halides, are known (JP 54/125,617 (1979)). However, these catalysts have the disadvantage that they act too unselectively and form a considerable amount of decarboxylated products, for example alkyl aryl ether and diaryl ether. Pure titanium dioxides, which are mainly used for pigment applications, are admittedly much more selective than mixed oxides of silicon and titanium but have very low activity.

It has now been found that rapid and nevertheless selective transesterification with the desired result can be achieved by means of titanium oxides having high inner surface areas. Virtually no carbon dioxide is eliminated, and the activity of the catalysts is retained even after multiple use.

Accordingly, the invention relates to a process for the preparation of carbonic diesters containing at least one aromatic ester groups from carbonic diesters containing at least one aliphatic ester group by catalysed transesterification with a phenol, which process is characterised in that the catalyst used is a titanium dioxide having a surface area of at least 20 $m^2/g$ as determined by the BET method in an amount of 0.1–200% by weight, relative to the carbonic diester used, which contains at least one aliphatic ester group.

Titanium dioxides in various crystalline modifications can be used, for example anatase and rutiles, anatase being preferably used. It is furthermore possible to use various metal oxides, for example those of Al, Zr, Ce, Nb, V, Sb, W and Mo and titanium dioxides doped with alkali metals. The titanium dioxide catalysts used have a surface area of at least 20 $m^2/g$ as determined by the BET method, preferably of at least 50 $m^2/g$ and particularly preferably of at least 90 $m^2/g$. The upper limit of the surface area can go up to 1000 $m^2/g$, in practice often up to 500 $m^2/g$. For some areas of application, it is advantageous and desirable to use titanium dioxides bound to solid supports. Only support materials which do not adversely affect the selectivity and the inner surface area of the titanium dioxide, for example stainless steel plates, honeycomb structures, expanded metals, sieves, can be used. The titanium dioxides to be used according to the invention are prepared from titanium-containing raw materials by conventional processes, for example by means of the sulphate process.

The titanium dioxide catalysts according to the invention are used in amounts of 0.1–200% by weight, preferably 1–100% by weight and particularly preferably 2–50% by weight, relative to the carbonic diester used, which contains at least one aliphatic ester group.

The catalysed transesterification according to the invention is understood to mean the exchange of one or two aliphatic ester groups for one or two aromatic ester groups. This can be, for example, the reaction of an aliphatic-aromatic carbonic diester with a phenol to give a purely aromatic carbonic diester, where the two aromatic ester groups may be different. Furthermore, it can be the reaction of a purely aliphatic carbonic diester with a phenol to give an aliphatic-aromatic or a purely aromatic carbonic diester. In this case, first one aliphatic ester group could be exchanged, for example by limiting the amount of phenol, and then the second aliphatic ester group could be exchanged, if desired for a different phenol, so that in this case two carbonic esters having two different aromatic ester groups are obtainable.

In the cases mentioned, the more volatile aliphatic ester alcohol is removed from the reaction mixture by distillation. Finally, the catalysed transesterification according to the invention can also be the disproportionation of a mixed aliphatic-aromatic carbonic diester to give a purely aromatic carbonic diester and a purely aliphatic carbonic diester which can also be separated off by distillation.

The phenol used for transesterification can also be a bisphenol.

In the case where a phenol is used for the transesterification, the weight ratio between the carbonic diester used, which contains at least one aliphatic ester group, and such a phenol can be varied within wide limits, for example from 1:99 to 99:1, preferably 1:9 to 9:1. In the case of a large excess of phenol, mainly the diaryl carbonate, and in the case of a large excess of purely aliphatic carbonic diester, preferably the mixed aliphatic-aromatic carbonic diester are formed. When bisphenols and at least 2 equivalents of carbonic diester are used, biscarbonates are formed which still contain aliphatic or aromatic monoester groups at the ends of the molecule. When approximately equivalent amounts of bisphenol and carbonic diester are used, monocarbonates having a free phenolic bisphenol hydroxyl group are first contained. Oligomeric or polymeric aromatic carbonates are formed therefrom under more vigorous reaction conditions. The differently substituted carbonic diesters can be separated from one another without difficulties, for example by distillation.

Carbonic diesters to be used according to the invention and containing at least one aliphatic ester group are those of the formula $$R^1O-CO-OR^2 \quad (I),$$

in which
R$^1$ and R$^2$, independently of one another, denote straight-chain or branched C$_1$–C$_{12}$-alkyl or C$_3$–C$_8$-cycloalkyl, in which furthermore R$^1$ can denote substituted or unsubstituted C$_6$–C$_{12}$-aryl.

Preferably, carbonic diesters of the formula $$R^3-O-CO-OR^4 \quad (II)$$

are used, in which
R$^3$ and R$^4$, independently of one another, denote straight-chain or branched C$_1$–C$_8$-alkyl, cyclopropyl, cyclopentyl or cyclohexyl, in which furthermore R$^3$ can denote substituted or unsubstituted phenyl.

Examples of straight-chain or branched C$_1$–C$_{12}$-alkyl are: methyl, ethyl, propyl, isopropyl, butyl, isobutyl, t-butyl, the isomeric pentyls, hexyls, octyls (inter alia 2-ethyl-hexyl), decyls and dodecyls, preferably one of the C$_1$–C$_8$-alkyls, particularly preferably one of the C$_1$–C$_4$-alkyls.

Examples of C$_3$–C$_8$-cycloalkyl are cyclopropyl, cyclopentyl, methyl-cyclopentyl, cyclohexyl, methylcyclohexyl, cycloheptyl or cyclooctyl, preferably cyclopropyl, cyclopentyl or cyclohexyl.

Examples of C$_6$–C$_{12}$-aryl are phenyl, biphenylyl or naphthyl, preferably phenyl. In the case of substitution of C$_6$–C$_{12}$-aryl, one or two substituents from the group comprising C$_1$–C$_4$-alkyl, C$_1$–C$_4$-alkoxy, cyano, fluorine, chlorine, bromine (chlorine is the preferred halogen) are suitable.

Examples of important carbonic diesters to be used and containing two aliphatic ester groups are: dimethyl carbonate, diethyl carbonate, dibutyl carbonate, diisopropyl carbonate, dicyclohexyl carbonate, dioctyl carbonate, preferably dimethyl and diethyl carbonate.

Examples of important aliphatic-aromatic carbonic diesters to be used are: methyl phenyl carbonate, ethyl phenyl carbonate, butyl phenyl carbonate, methyl cresyl carbonate and their homologs.

In the case where transesterification is carried out by means of a phenol, one of the formula (III)

is used, in which
denotes hydrogen, C$_1$–C$_4$-alkyl, C$_2$–C$_4$-alkenyl, C$_1$–C$_4$-alkoxy, C$_5$–C$_6$-cycloalkyl, phenyl, fluorine, chlorine, bromine or cyano;
R$^6$ represents hydrogen, C$_1$–C$_4$-alkyl, C$_2$–C$_4$-alkenyl, C$_1$–C$_4$-alkoxy, fluorine, chlorine, bromine and
R$^7$ represents hydrogen, C$_1$–C$_4$-alkyl or the group in which X denotes a single bond, —CH$_2$—, C$_2$–C$_5$-alkylene, C$_2$–C$_5$-alkylidene, C$_5$–C$_6$-cycloalkylene, C$_5$–C$_{10}$-cycloalkylidene, oxygen, sulphur, —CO—, —SO— or —SO—, in which R$^6$ and R$^7$ together can also denote a fused benzene ring.

Alkylene groups are linked to the aromatic rings via two different C atoms, i.e. in 1,2-, 1,3-, 1,4-, 1,5-, 2,3- or 2,4-linkage; alkylidene groups are linked to the aromatic rings via the same C atom, i.e. in 1,1-, 2,2- or 3,3-linkage. Cycloalkylene and cycloalkylidene can be mono- to trisubstituted by methyl or ethyl.

The monophenols used for transesterification in a preferred manner are those of the formula (IV)

in which
R$^8$ and R$^9$ independently of one another, denote hydrogen, C$_1$–C$_4$-alkyl or C$_5$–C$_6$-cycloalkyl, phenyl or chlorine.

Examples of phenols are:
unsubstituted phenol, o-, m- or p-cresol, o-, m- or p-chlorophenol, o-, m or p-ethylphenol, o-, m- or p-propylphenol, 2,6-dimethylphenol, 2,4-dimethylphenol and 3,4-dimethylphenol.

Preferred bisphenols are the of the formula (V)

in which
R$^{10}$ and R$^{11}$, independently of one another, denote hydrogen, C$_1$–C$_4$-alkyl, C$_2$–C$_4$-alkenyl, C$_1$–C$_4$-alkoxy, C$_5$–C$_6$-cycloalkyl, fluorine, chlorine or bromine, and
Y represents a single bond, —CH$_2$—, —C$_2$–C$_5$-alkylidene, C$_5$–C$_{10}$-cycloalkylidene, sulphur or —SO$_2$—.

The bisphenols used for transesterification in a particularly preferred manner are those in which X or Y and the hydroxyl groups are in the o,o',p,p' or o,p' position with respect to one another.

Very particularly preferred bisphenols are those of the formulae (VI)

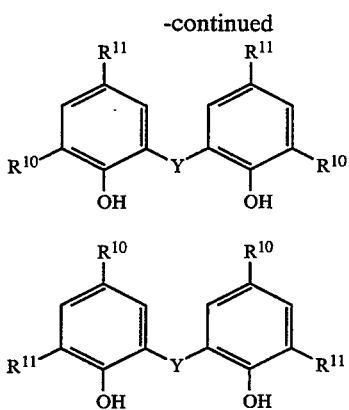

in which $R^{10}$, $R^{11}$ and Y have the abovementioned meaning.

Examples of bisphenols are: 2,2-bis(4-hydroxyphenyl)propane (=bisphenol A), bis-(4-hydroxyphenyl)methane, 1,1-bis(4-hydroxyphenyl)cyclohexane, 1,1-bis(4-hydroxyphenyl)-3,5,5-trimethylcyclohexane, 2,2-bis(3,5-dimethyl-4-hydroxyphenyl)propane, 2,2'- and 4,4'-dihydroxy-biphenyl, bis(5-methyl-2-hydroxyphenyl)methane, bis(3,5-dimethyl-2-hydroxyphenyl)methane, bis(3-tert.-butyl-5-methyl-2-hydroxyphenyl)methane. Of these, bisphenol A is particularly important.

Carbonic diesters obtainable according to the invention and containing at least one aromatic ester group are those of the formula

in which $R^{12}$ and $R^{13}$, independently of one another, represent substituted or unsubstituted $C_6$–$C_{12}$-aryl, which can be substituted in the above-mentioned manner, in which furthermore $R^{15}$ can denote straight-chain or branched $C_1$–$C_{12}$-alkyl or $C_3$–$C_8$-cycloalkyl.

The process according to the invention is carried out at a temperature of 50°–300° C., preferably 100°–250° C. The pressure is in principle not critical and can be in the wide range from 0.1–50 bar, preferably 1–20 bar, particularly preferably 1–15 bar.

According to the invention the reaction can be carried out without any solvent, i.e. in the melt of the substances to be reacted. However, it is likewise possible to work in a solvent which is inert with respect to the reaction. The procedure which uses such an inert solvent may be of importance, for example, if the alcohol formed by the transesterification can be more easily removed from the reaction mixture by means of such a solvent. Examples of solvents suitable according to the invention are:

aromatic (halogenated) hydrocarbons, such as toluene, xylenes, chlorobenzene, dichlorobenzenes, trimethylbenzenes, biphenyl, and (cyclo)aliphatic hydrocarbons, such as hexane, heptane, isooctane, cyclohexane, decalin, ligroin, petroleum ether, And aliphatic and aromatic nitriles and ketones, such as acetone, acetonitrile, acetylbenzene, benzonitrile and the like.

A possible procedure consists in bringing the transesterification mixture to the desired reaction temperature in an apparatus equipped with an adequate column and distilling off the aliphatic alcohol eliminated at the column head. In the case of disproportionation, in which the completely aromatic carbonic diester and the completely aliphatic carbonic diester are formed from an aliphatic-aromatic carbonic diester, the in general more volatile completely aliphatic carbonic diester can be distilled off at the column head. The more volatile substance can be separated off in the manner described by using an inert solvent or a gas stream. Furthermore, it is possible to initially introduce only a portion of one or both starting materials and meter the remainder into the melt or solution of the reaction mixture after the reaction has started.

In the case where a dialkyl carbonate is used, the alcohol eliminated can also be distilled off from the reactor together with some dialkyl carbonate; outside the reactor, alcohol and dialkyl carbonate are then separated, and the dialkyl carbonate is recycled into the reaction. This separation can be achieved by distillation or another separation process,, for example by adsorption on a molecular sieve.

The heterogeneous titanium dioxide catalysts can be separated off, after the transesterification reaction is complete, for example by filtration or by centrifuging, the additional use of inert diluents also being possible, for example in the reaction to give oligomeric or polymeric products. Likewise, it is possible to distill off the products formed directly from the non-volatile catalysts. The heterogeneous titanium catalysts can also be used in a continuous transesterification process in a stationary fixed bed as balls, rings, and the like, in which case it is of course not necessary to specifically separate off the catalyst.

EXAMPLES

Catalysts Used:

Catalyst I: PK 5585 (BAYER AG; finely divided titanium dioxide powder in anatase modification having a BET surface area of 270 to 330 m²/g, and a specific weight of 3.2±0.1 g/cm³) (according to the invention).

Catalyst II: PK 5585-1 (BAYER AG; finely divided titanium dioxide powder in anatase modification having a BET surface area of 90 to 110 m²/g, and a specific weight of 3.8±0.1 g/cm³) (according to the invention).

Catalyst III: Titanium dioxide pigment in anatase modification having a BET surface area of 7 m²/g (for comparison).

Catalyst IV: Titanium dioxide pigment in rutile modification having a BET surface area of 7 m²/g (for comparison).

EXAMPLES 1 to 8

General Experimental Procedure:

In order to determine the catalytic efficiency of the catalyst to be investigated under comparable conditions, a jacketed Soxhlet extractor comprising a multineck bottom flask, an extraction head (tube with inserted extraction thimble) and reflux condenser was used. A mixture of 0.25 mol of dialkyl carbonate and 0.50 mol of phenol was in each case heated to boiling in the bottom flask, so that the highly volatile dialkyl carbonate component distilled into the extraction head and evenly flowed through the extraction thimble filled in each case with 10 g of molecular sieve zeolite A, 4 Å in pore width (Baylith TE 144 from Bayer AG). A reaction temperature of 160° C. was reached. By adding the catalyst to be investigated (5 g each) to the bottom flask, the reaction was initiated (t=0), the alcohol of reaction formed was then entrained from the reaction mixture by means of the dialkyl carbonate and permanently bound to the molecular sieve. By determining the product formation as a function of the reaction time by gas chromatography (GC) analysis, the respective reaction rates were determined.

After completion of each transesterification experiment, the catalysts were separated off from the liquid reaction products by centrifuging, washed several times with dichloromethane, dried in vacuo and used for another experiment.

The results of experiments 1 to 8 clearly show the significantly higher activity of the titanium dioxide catalysts according to the invention compared with the standard anatase and futile catalysts III and IV. In contrast to JP 54/125,617, by-products were not found. It was found in particular that the catalysts according to the invention maintain their activity at a high level even after extended and repeated use, while the standard anatase and rutile types III and IV become completely deactivated after only a short time, i.e., after being re-used once or twice.

TABLE 1

| Example | Catalyst | Re-used | Dialkyl carbonate used[a] | t (h) | Product % by weight | formation[b] in % by area (GC) |
|---|---|---|---|---|---|---|
| 1 | I | fresh | DEC | 4 | 9.0 EPC | 1.2 DC |
| acc. to | | 1 × | DEC | 4 | 7.0 EPC | 0.8 DC |
| inv. | | 2 × | DEC | 4 | 6.5 EPC | 0.8 DC |
| | | 4 × | DEC | 4 | 6.5 EPC | 0.7 DC |
| 2 | II | fresh | DEC | 4 | 4.0 EPC | 0.5 DC |
| acc. to | | 1 × | DEC | 4 | 3.0 EPC | 0.4 DC |
| inv. | | 2 × | DEC | 4 | 2.8 EPC | 0.4 DC |
| | | 4 × | DEC | 4 | 2.8 EPC | 0.4 DC |
| 3 | III | fresh | DEC | 4 | 1.8 EPC | 0.05 DC |
| f. comp. | | 2 × | DEC | 4 | 0.2 EPC | — |
| 4 | IV | fresh | DEC | 4 | 0.6 EPC | 0.04 DC |
| f. comp. | | 2 × | DEC | 4 | 0.1 EPC | — |
| 5 | I | fresh | DMC | 1 | 2.0 MPC | — |
| acc. to inv. | | " | DMC | 4 | 11.8 MPC | 5.2 DC |
| 6 | II | fresh | DMC | 2 | 1.0 MPC | — |
| acc. to inv. | | " | DMC | 4 | 3.0 MPC | — |
| 7 | III | fresh | DMC | 2 | 0.4 MPC | — |
| f. comp. | | " | DMC | 4 | 1.3 MPC | — |
| 8 | IV | fresh | DMC | 2 | 0.1 MPC | — |
| f. comp. | | " | DMC | 4 | 0.3 MPC | — |

[a]DEC = diethyl carbonate, DMC = dimethyl carbonate
[b]DC = diphenyl carbonate, EPC = ethyl phenyl carbonate, MPC = methyl phenyl carbonate

We claim:

1. Process for the preparation of carbonic diesters containing at least one aromatic ester group from carbonic diesters containing at least one aliphatic ester group by catalysed transesterification with a phenol, characterised in that the catalyst used is a titanium dioxide having a surface area of at least 90 m²/g as determined by the BET method in an amount of 0.1 to 200% by weight, relative to the carbonic diester used, which contains at least one aliphatic ester group.

2. Process according to claim 1, characterised in that the catalyst is used in an amount of 1 to 100% by weight, relative to the carbonic diester used, which contains at least one aliphatic ester group.

3. Process according to claim 1, characterised in that carbonic diesters containing at least one aliphatic ester group of the formula $$R^1O\text{—}CO\text{—}OR^2$$

are used, in which $R^1$ and $R^2$ independently of one another, denote straight-chain or branched $C_1$-$C_{12}$-alkyl or $C_3$-$C_8$-cycloalkyl, in which furthermore $R^1$ can denote substituted or unsubstituted $C_6$-$C_{12}$-aryl.

4. Process according to claim 2, characterised in that the carbonic diesters contain at least one aliphatic ester group of the formula $$R^3O\text{—}CO\text{—}OR^4$$

in which $R^3$ and $R^4$, independently of one another, denote straight-chain or branched $C_1$-$C_8$-alkyl, cyclopropyl, cyclopentyl or cyclohexyl, in which furthermore $R^3$ can denote substituted or unsubstituted phenyl.

5. Process according to claim 1, characterised in that a phenol of the formula

in which $R^5$ denotes hydrogen, $C_1$-$C_4$-alkyl, $C_2$-$C_4$-alkenyl, $C_1$-$C_4$-alkoxy, $C_5$-$C_6$-cycloalkyl, phenyl, fluorine, chlorine, bromine or cyano;

$R^6$ represents hydrogen $C_1$-$C_4$-alkyl, $C_2$-$C_4$-alkenyl, $C_1$-$C_4$-alkoxy, fluorine, chlorine, bromine and $R^7$ represents hydrogen, $C_1$-$C_4$-alkyl or the group

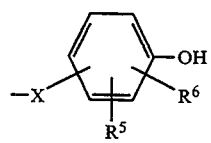

in which X denotes a single bond, —$CH_2$—, $C_2$-$C_5$-cycloalkylidene, oxygen, sulphur, —CO—, —SO— or —$SO_2$—, in which $R^6$ and $R^7$ together can also denote a fused benzene ring, is used for transesterification.

6. Process according to claim 1, characterised in that a phenol of the formula

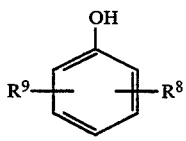

in which

R$^8$ and R$^9$, independently of one another, denote hydrogen, C$_1$-C$_4$-alkyl or chlorine, is used.

7. Process according to claim 1, characterised in that the phenol is a bisphenol of the formula

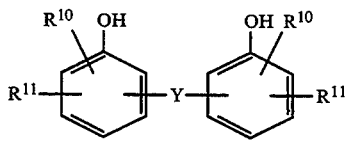

in which

R$^{10}$ and R$^{11}$, independently of one another, can denote hydrogen, C$_1$-C$_4$-alkyl, C$_2$-C$_4$-alkenyl, C$_1$-C$_4$-alkoxy, C$_5$-C$_6$-cycloalkyl, fluorine, chlorine or bromine, and Y represents a single bond, —CH$_2$—, —C$_2$—H$_5$-alkylidene, C$_5$-C$_6$-cycloalkylidene, sulphur or —SO$_2$—.

8. Process according to claim 1, characterised in that the reaction is carried out at a temperature of 50°-300° C.

9. Process according to claim 1 wherein the catalyst is used in an amount of 2 to 50% by weight relative to the carbonic diester used.

10. Process according to claim 1 wherein the reaction is carried out at a temperature of 100°-250° C.

* * * * *

UNITED STATES PATENT AND TRADEMARK OFFICE
CERTIFICATE OF CORRECTION

PATENT NO. : 5,354,923
DATED : October 11, 1994
INVENTOR(S) : Norbert Schon, et al.

It is certified that error appears in the above-indentified patent and that said Letters Patent is hereby corrected as shown below:

Col. 8, Line 3    Delete claim "2" and substitute -- 3 --

Col. 8, Line 64   After "$C_2$-$C_5$-" insert -- alkylene, $C_2$-$C_5$-alkylidene, $C_5$-$C_6$-cycloalkylene, $C_5$-$C_6$- --

Signed and Sealed this

Twenty-third Day of November, 1999

Attest:

Q. TODD DICKINSON

*Attesting Officer*   *Acting Commissioner of Patents and Trademarks*